United States Patent [19]

Barberi et al.

[11] Patent Number: 4,623,263
[45] Date of Patent: Nov. 18, 1986

[54] APPARATUS FOR THE THERMAL MEASUREMENT OF THE TEXTURE OF A POROUS BODY

[75] Inventors: Paul Barberi, Le Mesnil St. Denis; Pierre Bergez, Paris; Maurice Brun, Lyons; Michel Chevalier, Montlhery; Charles Eyraud, Lyons; Jean-Francois Quinson, Meyzieux, all of France

[73] Assignees: Commissariat a l'Energie Atomique; Centre Nationale de la Recherche Scientifique, both of Paris, France

[21] Appl. No.: 667,347

[22] Filed: Nov. 1, 1984

[30] Foreign Application Priority Data

Sep. 26, 1984 [FR] France .................... 84 14792

[51] Int. Cl.[4] ............... G01N 25/20; G01N 15/08
[52] U.S. Cl. ......................... 374/33; 374/31; 374/12; 374/25; 73/38
[58] Field of Search .............. 374/10, 11, 12, 13, 374/21, 25, 45, 31, 33, 54, 55, 56, 38, 115; 73/38, 73, 74, 75; 422/51; 436/5

[56] References Cited

U.S. PATENT DOCUMENTS

| | | | |
|---|---|---|---|
| 3,022,664 | 2/1962 | Stolwijk | 374/11 |
| 3,319,456 | 5/1967 | Speros et al. | 374/11 |
| 3,336,790 | 8/1967 | Nedumov | 374/11 |
| 3,379,061 | 4/1968 | Mercier | 374/10 |
| 3,456,490 | 7/1969 | Stone | 374/11 |
| 4,112,734 | 9/1978 | Goryachev | 374/11 |
| 4,130,016 | 12/1978 | Walker | 422/51 |
| 4,149,402 | 4/1979 | Manes | 73/23.1 |
| 4,383,770 | 5/1983 | Boschung et al. | 374/25 |
| 4,453,398 | 6/1984 | Demirel et al. | 374/45 |

FOREIGN PATENT DOCUMENTS

| | | | |
|---|---|---|---|
| 2856287 | 7/1980 | Fed. Rep. of Germany . | |
| 2479470 | 3/1980 | France . | |
| 0082436 | 7/1981 | Japan | 374/10 |
| 0206839 | 12/1982 | Japan | 374/11 |
| 2075675 | 11/1981 | United Kingdom . | |
| 0487318 | 10/1975 | U.S.S.R. | 374/10 |

OTHER PUBLICATIONS

Brun et al, "A New Method for the Simultaneous Determination of the Size and the Shape of Pores: the Thermoporometry", Thermochimica Acta, 21, 1977, pp. 59-88.

Primary Examiner—Charles Frankfort
Assistant Examiner—Thomas B. Will
Attorney, Agent, or Firm—Oblon, Fisher, Spivak, McClelland & Maier

[57] ABSTRACT

An apparatus for the thermal measurement of the texture of a porous body, including a measuring head, a measuring assembly and a processing and control circuit. The measuring head is provided with two identical cylindrical cells, a measuring cell and a reference cell, arranged in a furnace. The measuring assembly measures the mean temperature of the measuring cell, and measures a calorific effect in the measuring cell, and includes a calorific effect detector, a calibration circuit, a temperature regulator including a furnace heater. The measuring circuit supplies a temperature signal and a calorific effect signal to the processing and control circuit, which in turn controls the heater.

13 Claims, 6 Drawing Figures

APPARATUS FOR THE THERMAL MEASUREMENT OF THE TEXTURE OF A POROUS BODY

BACKGROUND OF THE INVENTION

The present invention relates to an apparatus for the thermal measurement of a texture of a porous body, called a thermoporometer. Porous bodies are used in numerous branches of industry and in general whenever an insoluble solid phase has to be intimately contacted with a fluid. This is the case with hydrocarbon synthesis or cracking catalysts, fillers introduced into elastomers or paints, pigments or absorbents used for the purification or chemical analysis (molecular sieves, absorbents for chromatography), hydraulic binders (cement), powders used in the preparation of emulsions (photographic emulsions, emulsions of products for agricultural treatments). Porous bodies are also used in separative methods such as ultrafiltration.

The methods used for studying the texture of a porous body are dependent on the size of the pores. For a diameter exceeding roughly 50 nanometers, it is necessary to use optical microscopic analysis methods. The invention relates to the study of the texture of porous bodies, whereof the pore radius is less than approximately 150 nanometers. Several methods for measuring the porosity of such porous bodies or substances are already known.

Thus, there are direct observation methods such as selectronic microscopy. This method makes it possible to directly observe the structure of the porous body, but is unfortunately difficult to perform in the case of mesoporous bodies, i.e. in which the average pore radius is between 2 and 50 nanometers.

There are also indirect methods based on the detection of capillary phenomena occurring in the porous bodies. These methods deduce the characteristics of the porous bodies either from the mechanical equilibrium of the surfaces (mercury porometry), or from the liquid - vapour thermodynamic equilibrium conditions of a condensate held within the porous body (Barrett, Joyner and Halenda or B.J.H. method).

The mercury porometry method described more particularly in "Powder Technology", vol. 29 - 1, May-June 1981, published by ElsevierSequoia, SA, Lausanne makes it possible to determine the porous distribution and deduce the specific surface. It consists of injecting mercury under high pressure into the porous body.

This method consists of measuring the variations in the apparent volume of the mercury-porous solid system subject to increasing pressures. From this is then deduced the distribution of the pore radii of the curve giving the pressure applied as a function of the injected mercury volume. The radii obtained are in fact the radii of the accesses to the porous cavities and not the radii of the actual porous cavities.

This method theoretically makes it possible to reach pores with a radius of 3 nanometers on using pressures close to 2.5 kbars. However, at these pressures, the texture of the porous body can be disturbed by crushing before the intrusion.

The B.J.H. method is a method for calculating the porous distribution based on the stepwise analysis of the desorption branch of the adsorption - desorption isotherm of a condensable vapour (nitrogen, argon, etc.). This method is described in detail in "The determination of pore volume and area distributions in porous substances. Computations from nitrogen isotherms" published in the Journal of the American Chemical Society, vol. 73, 1951, pp. 373-380.

As for the mercury porometry method, the disadvantage of this method is that it only gives information on the size of the access orifices to the pores and not on the size of the actual pores.

There is also an indirect method, called thermoporometry, described in particularly in the journal Thermochemica acta, no. 21, 1977, pp. 59 to 88. This method consists of a thermodynamic study of the liquid-solid and vapour phases of a fluid, which completely saturates a porous body. This study supplies a first relation making possible to calculate the size of the pores and subsequently to shape as determined the shape factor based upon the radii of the pores and in which the change of state has taken place from the variation between the temperature of the normal triple point of the free condensate and the temperature at which this change of state occurs in the pores. A second relation between the temperature and the apparent solidification or freezing energy measured in the pores makes it possible to calculate the corresponding porous volume.

With the aid of these relations and the solidification or freezing thermogram, which is the recording of the power given off by the freezing or solidification of the capillary condensate during a linear temperature drop it is possible to determine the distribution curve of the pore radii and the corresponding porous volumes.

This method is based on the fact that the equilibrium conditions of the solid, liquid and gaseous phases of a pure substance in a highly divided state are a function of the curvature of the interfaces. In the case of a fluid contained in a porous body, the curvature of the solid - liquid interface is imposed by the pores size. The freezing or solidification temperature is consequently different in each pore of the material.

The solidification thermogram of a known condensate in an unknown porous body consequently permits the determination of the size of the pores by the measurement of the solidification temperature or freezing point and the volume of said pores by measuring the state change energy. Thus, this method gives the real size of the pores and not that of the access orifices thereof, as in the case of the B.J.H. and mercury porometry methods.

More specifically, in the thermoporometry method, at each temperature freezing takes place in the pores of a given size. Knowing the apparent solidification of freezing energy. the volume of these pores is determined by a calorimetric measurement of the energy released at this temperature. Thus, the pore radius distribution curve is directly deduced from the solidification of freezing thermogram.

The known thermal measuring equipment realizing the aforementioned method are generally calorimeters designed for making precise heat quantity measurements. On such equipment, the temperature measurement is of a secondary and not very accurate nature.

However, this temperature measurement is vital in thermoporometry, because it forms the basis for the method for calculating the pore radii. In the known equipment, the difficulties of checking or controlling the temperature consequently make it impossible to obviate the surface of the fluid in which the porous body is immersed during the temperature drop. As a function of the fluids used, this supercooling range has a varying significance. It can reach 10° C., and more in the case of water. Thus, the supercooling range limits the use of the solidification or freezing thermogram.

SUMMARY OF THE INVENTION

The object of the present invention is an apparatus for the thermal measurement of the texture of a porous body able to very accurately measure and check the temperature. Thus, it is possible to have a thermal cycle preventing supercooling during the linear temperature drop. This makes it possible to utilize the solidification thermogram even with porous body samples having very large pore radii, e.g. up to 150 nanometers. This represents an important improvement compared with conventional equipment of the calorimeter type, whose analysis range was limited to porous bodies with pores of less than 10 nanometers.

More specifically, the present invention relates to an apparatus for the thermal measurement of the texture including the radius and shape of the pores of a porous body having a measuring head, a measuring assembly and a processing and control means, said measuring head being provided with two identical cylindrical cells, a measuring cell and a reference cell, arranged in a furnace, wherein the measuring assembly comprises means for measuring the temperature of the measuring cell, means for measuring a calorific effect in the measuring cell, said means being constituted by a calorific effect detection means and a calibration means, as well as temperature regulating means comprising a furnace heating means.

In a preferred manner, the signal supplied by the temperature measuring means is calibrated by means of reference substances.

According to a preferred embodiment, each cell comprises a generally cylindrical support, the measuring cell support receiving the porous body to be studies, and a first thermoresistive winding outside said support and concentric thereto, each first thermoresistive winding being connected to the temperature measuring means.

Preferably, the means for detecting the calorific effect in the measuring cell comprises a temperature detection means for each cell and means for measuring the temperature or thermal unbalance between these cells.

According to a preferred embodiment, the temperature detection means of each cell is constituted by a second thermoresistive winding, outside and concentric to the first thermoresistive winding, said second thermoresistive windings being connected to the temperature unbalance measuring means.

According to another preferred embodiment, each cell has a single thermoresistive winding for measuring the temperature and detecting the calorific effect.

Preferably, the calibration means produces by the Joule effect a calorific effect of known regulatable level in the measuring cell.

According to a preferred embodiment, each cell comprises a third thermoresistive winding external and concentric of the two other thermoresistive windings, said third thermoresisitve winding being connected to the calibration means.

According to a preferred embodiment, the processing and control means ensures a thermal regulation of the furnace by controlling the heating means in order to maintain the temperature measured by the furnace temperature measuring means, or the temperature measured by the means for measuring the temperature of the measuring cell and the reference temperature $T_c$.

In a preferred manner, the processing and control means is able to perform the following successive stages:

linear or non-linear drop of the furnace temperature to the solidification or freezing of the fluid contained in the pores of the porous body;

inversion of the temperature variation up to the partial melting the excess fluid;

linear or non-linear temperature drop to the complete solidification of freezing of the fluid;

these stages being optionally separated by temperature zones for preventing the propagation of thermal shocks.

These stages make it possible to prevent supercooling and consequently to provide a solidification thermogram which can be used for both very large and very small pores.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENTS

Figure 1:
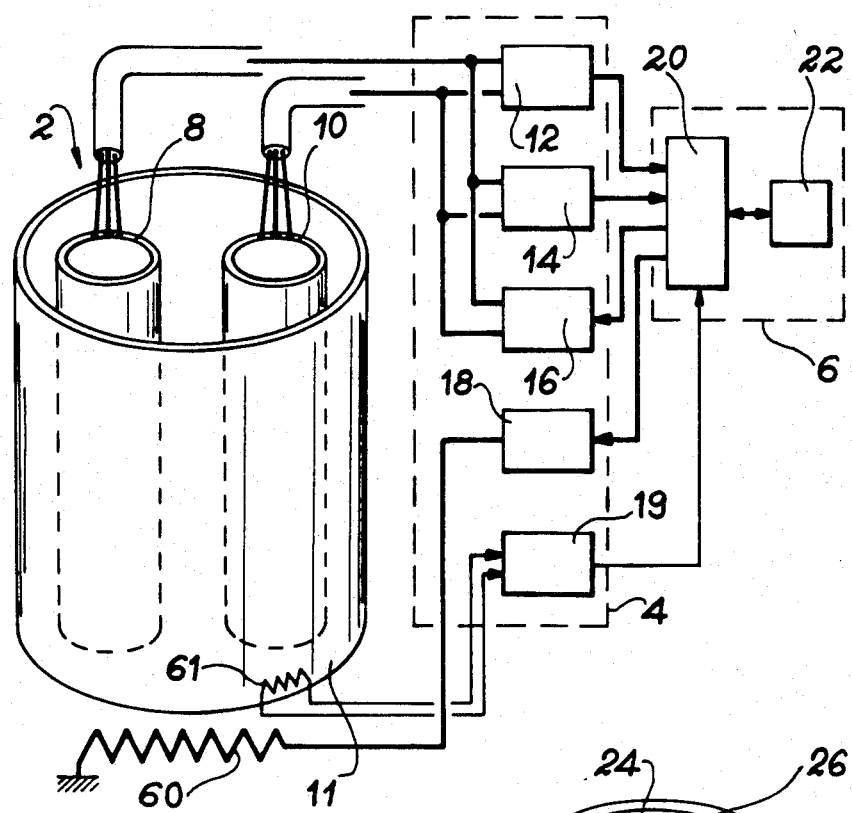
FIG. 1 is a diagrammatic representation of the thermal measuring apparatus according to the invention.

FIG. 1 diagrammatically shows the thermal measuring apparatus according to the invention, which comprises three parts, namely a measuring head 2, a measuring assembly 4 and processing and control means 6. The measuring head 2 is a differential heat sensor having two cylindrical, identical cells 8 and 10 arranged in a furnace or oven 11. One of the cells is a measuring cell containing the saturated porous body and immersed in a fluid, whilst the other is a reference cell. The furnace comprises a heating resistor 60. It may also comprise a sensor, such as a thermoresistor 61.

The measuring head is generally placed in a cryostat, so as to reach the requisite temperature (at least −40° C. if the fluid is water and −60° C. if the fluid is benzene). Different conventional cryostats can be used, such as the liquid oxygen or nitrogen immersion cryostat, the freon compressor evaporation cryostat, refrigerator liquid cryostat or the Peltier effect cryostat, each of these means being usable singly or in combination.

Cells 8 and 10 are electrically connected to a measuring assembly 4, which comprises a temperature measuring means 12, a means 14 for measuring the temperature unbalance between the two cells, said means being an element of a means for detecting a calorific effect in the measuring cell, a calibration means 16 and a furnace heating means 18. The measuring assembly can also comprise a means 19 for measuring the furnace temperature. Each means of the measuring assembly 4 is connected to the processing and control means 6. The latter comprises calculating or computing means 20, e.g. a microprocessor system with peripheral display and printing means 22.

The temperature measuring means 12 supplies to the calculating means 20 the temperature of the cell containing the porous body of measuring head 2. On its return, this signal can be used by the calculating means 20 for controlling the heating means 18, in order to keep the temperature of cells 8, 10 at a reference value. The temperature regulation can also be carried out for the furnace, as a function of the signal supplied by means 19.

Means 14 supplies the calculating means 20 with a signal representing the release or absorption of heat produced by the change of state of the fluid during a temperature variation. The calibration means 16 can give off a known heat quantity to the measuring cell, e.g. by the Joule effect. This makes it possible to calibrate the signal supplied by means 14. This calibration means is of interest in that it permits the calibration at any temperature, i.e. a continuous calibration. However, the apparatus can also operate with a discontinuous calibration, e.g. of the type in which a sample of a known substance is introduced into the measuring cell which, by melting, gives off a known heat quantity. The apparatus is then calibrated for the melting temperature of said known substance.

The operation of the apparatus according to the invention requires precise knowledge of the temperature of the porous body. Thus, without a calibration, it is impossible to accurately determine the pore radius as a function of the state change temperature of the condensed fluid. The need to accurately know the temperature is made readily apparent from the following example. In the case where the fluid is water, the pore radius $R_p$ is linked with a temperature variation $\Delta\theta$ by the following relation:

$$R_p = -(64.67/\Delta\theta) + 0.57 \text{ with } 0° C. > \Delta\theta > -40° C.$$

The presence of pores with a radius of 50 nanometers consequently leads to a temperature variation $\Delta\theta$ of 1.3° C. An uncertainty of 0.026° C. on this temperature variation leads to an uncertainty of 1 nanometer on the size of the pores.

In order to calibrate the apparatus, use is consequently made of a method consisting of the study of the calorific effect resulting from the melting of the different reference bodies at variable temperature sweep rates or speeds. Several different temperature sweep cycles can be exploited by the processing and control means.

The study of the calorific effect produced during each temperature sweep cycle makes it possible in known manner to determine the coefficients making it possible to calculate the pore radius and pore volume of the porous body analyzed.

When the apparatus is calibrated, a solidification or freezing thermogram is obtained linking the heat quantity given off as a function of a linear temperature variation. The distribution curve (dV/dR), in which V is the pore volume and R the pore radius is then determined in known manner. It is difficult to obtain the solidification thermogram with known equipment, because a supercooling phenomenon generally appears during the temperature drop, which limits the method to pores with a size less than 30 nanometers.

In order to obviate this disadvantage, according to the invention the following procedure is adopted:

1. The furnace is rapidly cooled until the condensate solidifies and the cooling rate can reach 100° C./hour or more.
2. The porous body is reheated in a controlled manner up to the start of melting of the excess fluid. The reheating rate is approximately 0.7° C./h to 30° C./h. It is dependent on the accuracy required for measuring the largest pores. Thus, the larger the pores, the more it is important to slow down the temperature variation speed, so that on the one hand the thermodynamic balance is effected at each instant and on the other that the response time of the calorimeter does not disturb the thermogram.
3. Cooling takes place in a controlled manner until the fluid completely solidifies. This cooling takes place with the same precautions as the reheating of the preceding stage.

The difficulty of the process is that it is necessary to keep a little condensate solidified in excess at the start of solidification according to point 3., said solidified condensate acting as a nucleus for the final solidification. This difficulty is overcome in the apparatus according to the invention, through the possibility of accurately checking or controlling the temperature of the sample of the porous body.

A description will now be given of an embodiment of each of the means of the apparatus of the invention.

Figure 2:
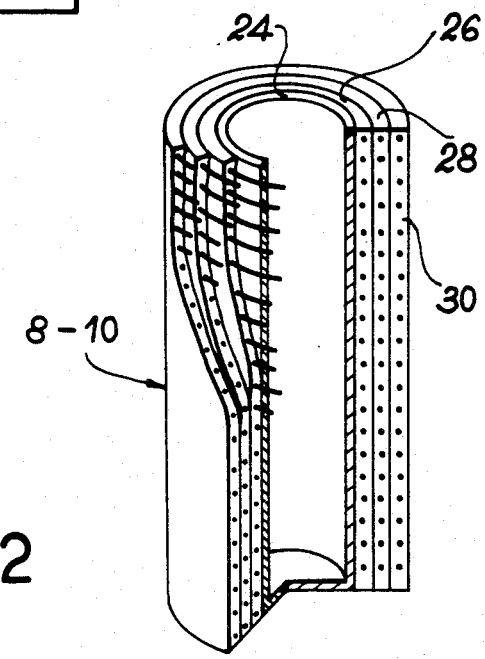
FIG. 2 is a perspective view partially in cross-section diagrammatically illustrating the structure of a cell of the measuring head of the apparatus of the invention.

FIG. 2 illustrates an embodiment of the measuring head cells. Each cell comprises a metal sleeve 24 forming a support. The measuring cell receives in the said support a scoop containing the porous body to be studied saturated and immersed in the condensate. Preferably, this sleeve has a cylindrical, elongated shape, which permits a better thermal homogeneity.

Several thermoresistive windings are concentrically arranged around the sleeve 24. The innermost winding is the first thermoresistive winding 26, which is connected to the temperature measuring means 12. Around the first winding is arranged a second winding 28, which is connected to the means 14 for measuring the thermal unbalance between the cells. Finally, a third winding 30 is connected to a calibrating means 16.

According to another not shown embodiment, the cell may only have two thermoresistive windings, the first being used for the temperature measurement and for the temperature unbalance measurement and the second for calibrating the calorific effect.

The various elements constituting the cell are designed or chosen by the expert on the basis of numerous criteria, such as a temperature range of 80° C. to 100° C., thermally neutral construction materials, a compatibility between the thermal and mechanical characteristics of the different elements, a high sensitivity of the detecting elements, a very good constructional symmetry (thermal, mass and electrical ) and a low thermal inertia.

Preferably, the two cells are completely identical (material, number of thermoresistive windings, etc.), so as to be less sensitive to parasitic effects.

Figure 3:
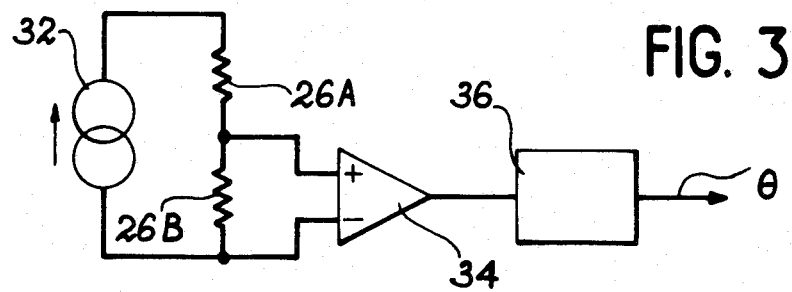
FIG. 3 is a circuit diagram of an embodiment of the temperature measuring means associated with the first thermoresistive winding.

In order to measure the temperature of the porous body with the necessary accuracy, the temperature measuring means 12 performs an absolute temperature measurement of the measuring cell containing the porous body and the condensate. FIG. 3 illustrates an embodiment of this temperature measuring means associated with the first thermoresistive winding of each cell.

This means comprises a current generator 32, which supplies the first thermoresistive winding $26_A$, $26_B$ of the reference cell and the measuring cell. These two windings are connected in series and are traversed by the same current. Thus, the two cells are placed under identical conditions. Moreover, this makes it possible to use one or other of these cells as desired, for the said measurement. The voltage at the terminals of the thermoresistive winding 26B of the measuring cell is detected by a differential amplifier 34. The latter is followed by an integrator 36, which supplies a signal representing the temperature of the cell.

Figure 4:
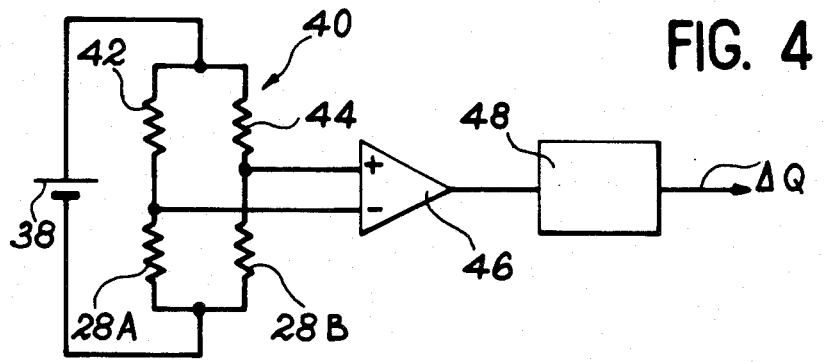
FIG. 4 is a circuit diagram of an embodiment of the calorific effect detection means.

FIG. 4 shows an embodiment of the means 14 for measuring the temperature or thermal unbalance between the two cells. This means makes it possible to measure the heat given off or absorbed by the change of state of the condensate. This measuring means comprises a d.c. voltage generator 38 supplying a resistor bridge 40, a differential amplifier 46 and an integrator 48, which supplies a signal representing the calorific effect $\Delta Q$. The resistor bridge comprises two rows of resistors in parallel supplied by generator 38. The first row comprises a resistor 42 in series with thermoresistor 28A, of the second thermoresistive winding of the reference cell. The second row of resistors comprises a resistor 44 in series with the second thermoresistive winding 28B of the measuring cell. The common point of the resistors 42 and 28A on the one hand and the common point of resistors 44 and 28B on the other are connected to the two inputs of amplifier 46. This differential arrangement makes it possible to reach a detection threshold better than 10 $\mu W$.

Figure 5:
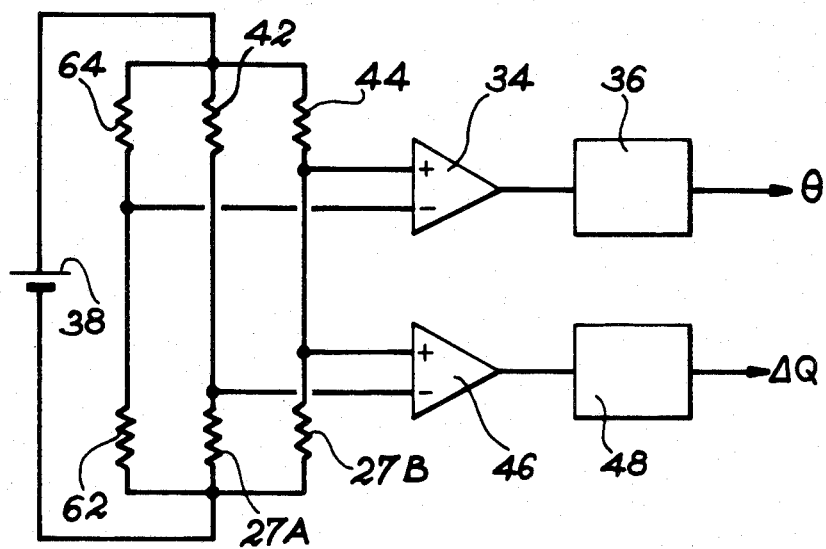
FIG. 5 is a circuit diagram of an embodiment of the temperature measuring means and the calorific effect detection means.

FIG. 5 shows a constructional variant in the case where each cell only has two thermoresistive windings, it being used simultaneously for measuring the temperature in the measuring cell and for measuring the thermal unbalance between the two cells. In FIG. 5, this thermoresistive winding carries resistor 27A for the reference cell and resistor 27B for the measuring cell.

In FIG. 5, the elements identical to those of FIG. 4 carry the same references. The measurement of the calorific effect is obtained by a device identical to that of FIG. 4. Conversely, the measurement of the temperature is obtained in a different way to that of FIG. 3. A resistor 62 having a known fixed value is connected in series with a resistor 64, identical to resistors 42, 44. The group of resistors 62, 64 is connected in parallel with the resistors 44, 27B and 42, 27A. At its noninverting input, differential amplifier 34 receives the signal supplied by the common point of resistors 27B, 44 whilst at its inverting input it receives the signal supplied by the common point of resistors 62, 64. Resistor 62 makes it possible to compensate the drift of the apparatus in the temperature measurement.

Means 14 for measuring the thermal unbalance between the cells and the thermoresistive windings associated therewith and shown in FIGS. 4 and 5 can be replaced by a conventional heat flow measuring means, of the thermobattery fluxmeter type. This differential thermocouple arrangement suffers from the disadvantage of a physical connection between the two cells. Thus, preferance is given to the use of a measuring means according to FIGS. 4 and 5, which is not very expensive, sensitive, has no coupling, suffers from no aging and has a good symmetry.

Figure 6:
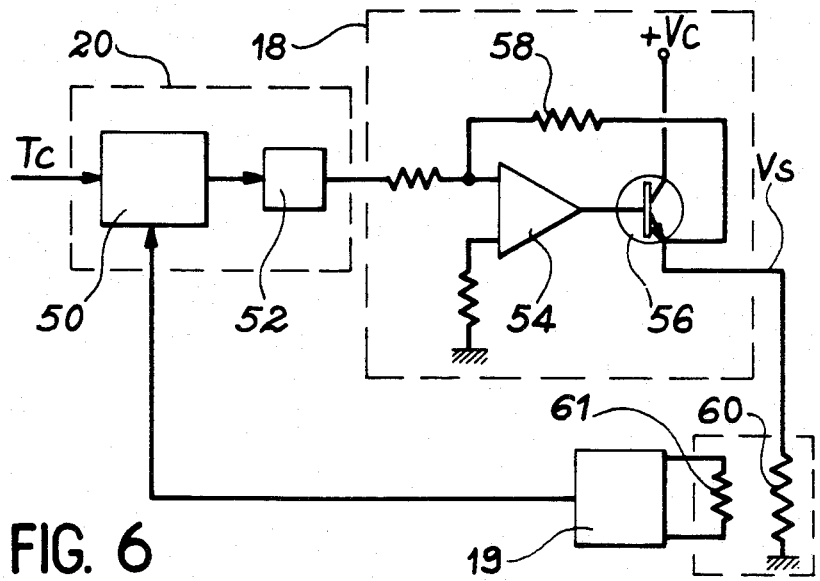
FIG. 6 is a circuit diagram of an embodiment of the heat regulation means.

FIG. 6 shows the thermal regulating chain of the furnace of the apparatus according to the invention. This is constituted by a computer 50, receiving on the one hand a reference temperature and on the other the temperature obtained by the furnace temperature measuring means. The computer supplies a digital signal, which is converted into an analog signal by a digital - analog converter 52. The computer and the digital - analog computer are two elements of calculating or computing means 20.

The signal supplied by the analog - digital computer 52 is received by the heating means 18, which essentially comprises a differential amplifier 54, a power transistor 56 and a negative feedback resistor 58. The inverting input of amplifier 54 is connected to the output of the digital - analog converter 52, its output being connected to the base of the transistor 56. The collector of the latter receives a d.c. supply voltage $V_C$ and supplies at its emitter a voltage $V_S$. The negative feedback resistor 58 is connected between the inverting input of amplifier 54 and the emitter of transistor 56. The emitter of transistor 56 is connected to the heating resistor 60 of the furnace.

This temperature is detected by a sensor 61, e.g. a thermoresistor and is then converted into a temperature level by means 19. This temperature can also be detected by the first thermoresistive winding 26B of the measuring cell and is converted by means 12, instead of sensors 61 and means 19.

The reference value $T_C$, which is compared with computer 50 with the value supplied by means 12 or 19 is dependent on numerous parameters, including the temperature sweep rate, the weight of the sample of the porous body introduced into the measuring cell, the nature of the condensing fluid used as well as the different calorimetric constants of the measuring head elements.

Regulation by the thermoresistive winding 26B assures a better thermal regulation of the cells. However, it is difficult to put into effect as a result of the response time of the cells. Regulation by sensor 61 is simpler.

What is claimed is:

1. An apparatus for thermal measurement of the texture of a porous body subjected to thermal gradients, having a measuring head, a measuring assembly and a processing and control means, said measuring head being provided with two identical low inertia cylindrical cells, including a measuring cell and a reference cell wherein at least one of said two cells are in contact with said porous body and, wherein the measuring assembly comprises:

a mean temperature measuring means for measuring the mean temperature of the measuring cell, while said porous body is subject to said temperature gradient and before said porous body reaches thermal equilibrium said mean temperature measuring means delivering a signal to the processing and control means in order to calculate the radius and shape of pores under examination;

a calorific effect measuring means for measuring a calorific effect in the measuring cell, said calorific effect measuring means delivering a signal to the processing and control means in order to calculate the pore volume, said calorific effect measuring means comprising a calorific effect detection means and an electrical calibration means; and a temperature regulation means comprising a furnace for heating said measuring head and a cryostat for cooling said measuring head.

2. An apparatus according to claim 1, wherein each cell comprises a generally cylindrical thin support, and a first thermoresistive winding outside said support and concentric thereto, each first thermoresistive winding being connected to the mean temperature measuring means.

3. An apparatus according to claim 2, wherein the calorific effect detection means for detecting the calorific effect in the measuring cell comprises, on each cell, a thermal unbalance measuring means and a second thermosresistive winding, external of and concentric to the first thermoresistive winding, said second thermoresistive winding being connected to said thermal unbalance measuring means.

4. An apparatus according to claim 3, wherein each cell comprises a third thermoresistive winding, external of and concentric to the two other thermoresistive windings, said third thermoresistive winding being connected to the electrical calibration means.

5. An apparatus according to claim 1, wherein each cell comprises a generally cylinder thin support and a single thermoresistive winding outside said support and concentric thereto, said thermoresistive winding being connected to the mean temperature measuring means and to the calorific effect detection means.

6. An apparatus according to claim 5, wherein each cell comprises another thermoresistive winding, external of and concentric to the first thermoresistive winding, said another thermoresistive winding being connected to the electrical calibration means.

7. An apparatus according to claim 1, wherein the cryostat is a Peltier effect device.

8. An apparatus according to claim 1, wherein the processing and control means ensures a heat control of the furnace and comprises means for controlling the heating means in order to maintain the mean temperature of the reference cell at a programmed reference value.

9. An apparatus according to claim 8, wherein the reference cell comprises a generally cylindrical thin support, and a thermoresistive winding outside said support and concentric thereto, said thermoresistive winding detecting the mean temperature of the reference cell and supplying said mean temperature to the processing and control means.

10. An apparatus according to claim 9, wherein the programmed reference value takes into account of temperature scanning rate and of weight of the sample of the porous material studied.

11. An apparatus according to claim 1, wherein the processing and control means is able to perform the following successive stages:
  linear or non-linear drop in the furnace temperature up to the solidification of the fluid contained in the pores of the porous body;
  inversion of the temperature variation up to the partial metling of the excess fluid;
  automatic inversion of the temperature variation before the end of the melting of the excess fluid and linear or non-linear to the complete solidification of the fluid;
  said stages making it possible to prevent supercooling of the condensate.

12. An apparatus according to claim 11, wherein the processing and control means is able to control temperature zones between each stage in order to allow heat shocks damping.

13. The apparatus according to claim 1, wherein said mean temperature measuring means comprises a differential amplifier for receiving an output from said measuring cell and said reference cell and a integrator for receiving the output from said differential amplifier wherein the output of said integrator is a signal representing the temperature of said measuring cell.

* * * * *